United States Patent [19]

Boer

[11] 4,010,759
[45] Mar. 8, 1977

[54] INSULATED, CORROSION RESISTANT MEDICAL ELECTRONIC DEVICES AND METHOD FOR PRODUCING SAME

[75] Inventor: Gerard B. M. Boer, Dieren, Netherlands

[73] Assignee: Vitatron Medical B.V., Dieren, Netherlands

[22] Filed: Aug. 29, 1975

[21] Appl. No.: 608,894

[52] U.S. Cl. .................. 128/419 P; 128/419 PS; 174/50.61; 174/110 A; 174/152 GM
[51] Int. Cl.² ........................................ A61N 1/36
[58] Field of Search ............... 128/404, 418, 419 C, 128/419 E, 419 P, 419 PS, 419 R, 421, 422; 174/110 A, 152 GM, 50.61

[56] References Cited
UNITED STATES PATENTS

| | | | |
|---|---|---|---|
| 3,275,901 | 9/1966 | Merritt et al. | 174/50.61 |
| 3,557,796 | 1/1971 | Keller, Jr. et al. | 128/419 PG |
| 3,866,616 | 2/1975 | Purdy et al. | 128/419 PS |
| 3,888,260 | 6/1975 | Fischell et al. | 128/419 PS |
| 3,926,198 | 12/1975 | Kolenik | 128/419 P |

FOREIGN PATENTS OR APPLICATIONS

| | | | |
|---|---|---|---|
| 2,056,493 | 5/1972 | Germany | 128/419 P |
| 906,831 | 9/1962 | United Kingdom | 174/110 A |
| 1,274,882 | 5/1972 | United Kingdom | 128/419 P |

*Primary Examiner*—William E. Kamm
*Attorney, Agent, or Firm*—Woodcock Washburn Kurtz & Mackiewicz

[57] ABSTRACT

An insulated, corrosion-resistant heart pacer is described which incorporates a novel tantalum output means, said output means having disposed on at least the exterior surfaces thereof an anodically-formed substantially continuous $Ta_2O_5$ insulating layer. The output means of the pacer or other medical electronic device comprises a tantalum centerpin disposed through a hermetically sealed titanium case, which centerpin is welded to a tantalum feed wire, the combination providing a device in which the $Ta_2O_5$ insulating layer reduces the electrical leakage from the tantalum conductor to the titanium case, and whereby the insulating layer disposed thereon further protects the pacer from electrolysis and electrochemical corrosion. An alternate embodiment of the present invention provides tantalum conduit means for electrically connecting an energy source to logic circuitry which is disposed within a hermetically sealed titanium case. Finally, a method is provided for producing and utilizing tantalum, titanium, aluminum, hafnium, niobium, and like metals, which comprises the step of forming a continuous oxidation layer of components of such metals, which method of forming includes the steps of immersing the output means in an electrolytic solution and applying a positive voltage to the tantalum or like material to anodically form a $Ta_2O_5$ or corresponding insulating layer thereon. As a result, a corrosion resistant insulated heart pacer is provided having better insulation against the effects of electrolysis and electrochemical corrosion, as well as one in which discharge of the energy source is minimized.

34 Claims, 5 Drawing Figures

INSULATED, CORROSION RESISTANT MEDICAL ELECTRONIC DEVICES AND METHOD FOR PRODUCING SAME

BACKGROUND OF THE INVENTION

The present invention relates generally to the field of medical electronic devices, and more particularly, to the field of implantable heart pacers which are substantially encapsulated in epoxy.

Generally, heart pacers are comprised of electronic circuit means for producing a suitable heart muscle stimulating output pulse and output means for conducting the said output pulse from the electronic circuit means to said heart muscle. Normally, an electrode is connected at one end into the particular heart muscle to be stimulated and at the other to a pacer which has been implanted or imbedded subcutaneously in the patient's chest, abdomen or other suitable location. With implantation of the heart pacer subcutaneously come various secondary problems which should be overcome in designing a safe and reliable heart pacer. Of particular importance is the insulation of a heart pacer firstly to protect the patient from internal contamination of the body from the materials used in the heart pacer, and secondly to protect the materials used in the heart pacer from detrimental corrosive attack by the body fluids which are prevalent in the implantation area.

In the past, heart pacers having been produced which encapsulate miniature circuitry within an envelope of epoxy. Other materials, such as plastics, silicon rubber and TEFLON(registered Trademark), have also been used for isolating purposes. Generally, these epoxy envelopes comprise rounded packets having formed therein an inert grounding plate for making electrical contact with the body and a negative output terminal for contacting the output electrode which is embedded in the heart muscle to be stimulated. Otherwise, the opoxy forms a smooth continuous insulating barrier between the body fluids which surround the heart pacer and the energy source and circuitry which together comprise the electronic circuit means for producing the desired rhythmic heart muscle stimulating negative output pulse.

Unfortunately, while providing a reasonable insulation of the body from the electronic circuit means of the heart pacer, encapsulation of a heart pacer with epoxy has not proven to be sufficient in insulating the various components of the heart pacer from the corrosive attack of the surrounding body fluids. Although there are, of course, a multiplicity of chemical constituents in the body fluids surrounding the implanted pacer, for the purposes of this discussion it suffices to consider these fluids as being comprised mainly of an aqueous sodium and potassium chloride salt solution. In the past, a certain amount of difficulty has been encountered in producing pacers due to the phenomenon which is experienced when an epoxy encapsulated pacer is immersed for extended periods of time in such a solution. In particular, it has been found that the relatively small water molecules in that solution tend to penetrate the epoxy and to come in contact with the wires and other electrical components encapsulated therein. Even though the maximum voltage normally present within the pacer is normally within the range of 4–8 volts, and almost always less than 15 volts, this voltage is nonetheless sufficient to cause the electrolysis of water molecules contacting charged conductors. When positive and negative electrode components are positioned within a space containing an electrolyte, oxygen gas is formed at the positive electrode and hydrogen gas is formed at the negative electrode. Since, in the event of electrolysis, this gas is formed in a relatively confined area around the charged conductors and within the capsule, tremendous internal pressures could be created during the operation of the pacer, which pressures would have to be vented. This condition can be even more serious with the use of large surface integrated circuits in cans. Further, the larger the components, the greater the chance of breaking or cracking of the epoxy due to differences in expansion coefficients.

In prior art designs, batteries were often encapsulated within the epoxy capsule in close proximity to the electronic circuitry which produced the rhythmic pacer output pulse. Although the disposition of the energy source next to the electronic circuitry tended to reduce the length of the leads which were required to connect the energy source to the logic circuitry in the pacer, this juxtaposition tended to increase the likelihood that leakage of battery electrolytes from the energy source would damage or destroy the logic circuitry and/or the function of the device. Ions which cause electrolysis and electrochemical corrosion can also originate from leaky batteries, as for example, the normally used non-hermetically sealed mercury batteries. When it is remembered that pacers are normally implanted for extended periods during which their operation must be virtually infallible, it may be seen that any instances of malfunction which are caused by electrolyte leakage are not tolerable. Therefore, in order to overcome the problem that electrolyte leaking from a battery disposed near the logic circuitry of a pacer would be conducted along the conduit leading from the battery to the logic circuitry, various means have been employed in order to minimize the possibility that electrolyte will be transmitted to the interfere with the operation of the pacer's logic circuitry. In particular, leads have been employed which have a generally spiral or helical configuration which are intended to prevent the transmittal of electrolyte from the battery to the logic circuitry.

SUMMARY OF THE INVENTION

The present invention utilizes a hermetically sealed titanium case in combination with a tantalum output means which provides a connection through the lid of the case. Prior to sealing the lid to the case, the lid and output means are aniodically oxidized so as to form an insulating oxide layer on each. In one alternate embodiment of the present invention, the energy source of the heart pacer is disposed outside of the hermetically sealed titanium case and is connected to the logic circuitry disposed within that case by a tantalum conduit means also having an anodically formed continuous $Ta_2O_5$ layer disposed on the surfaces thereof. Additionally, a method of assembling a heart pacer in accordance with either of the preferred embodiments of the present invention is provided wherein the helical tantalum wire and tantalum centerpin are welded to each other prior to a forming step in which the tantalum components are subjected to positive voltages in the range of 10 to 140 volts. This aniodic, or anodic formation of the $Ta_2O_5$ coating produces a substantially continuous insulating layer on the tantalum components which acts to reduce electrical leakage to an infinitesimal amount. Additionally, the $Ta_2O_5$ coating is virtually impervious to corrosive attack from leaking battery electrolytes, as well as from the hydroxides of sodium and potassium which might otherwise have naturally deteriorated the material.

Not only has applicant provided a tantalum conduit means which has the capacity to repair minor imperfections in the tantalum oxide coating during the operation of the heart pacer, but applicant has also discovered that the aniodic formation of the negative output means of the present invention results in an electrical leakage from the output means which is approximately one thousand fold less than that which would normally be encountered using a bare tantalum negative output wire.

In addition to the above, the present invention provides for the easy encapsulation of the hermetically sealed titanium case within an epoxy capsule means while providing a pacer which is not prone to malfunction by reason of discharge and/or corrosive attack resulting from battery electrolyte leakage. Finally, as discussed above, the provision of the novel tantalum oxide insulating layer on the surfaces of the input and output means of the present invention allows for the encapsulation of these means within the epoxy capsule without danger of malfunction resulting from electrolysis of water which penetrates the epoxy material.

Consequently, it is a primary object of the present invention to provide a heart pacer and method of making same which is better insulated against electrical leakage.

Another object of the present invention is to provide a heart pacer encapsulated in an epoxy material wherein the likelihood of malfunction resulting from electrolysis is virtually eliminated.

A further aim of the present invention is the provision of an electronic stimulating device which is resistant to electrochemical corrosion caused by leaking battery electrolyte.

A further aim of the present invention is the provision of a heart pacer in which the insulating layer on the positive input means is self-repairing.

A yet further aim of this invention is the provision of a electronic stimulating device having an output terminal from which are provided stimulus signals which are negative relative to the device case, and wherein the case has at least a portion thereof adjacent to the output terminal which has a pre-oxidized insulating layer.

These and other objects of the present invention will become apparent from the following more detailed description of the present invention.

DETAILED DESCRIPTION OF THE DRAWINGS

Figure 1:
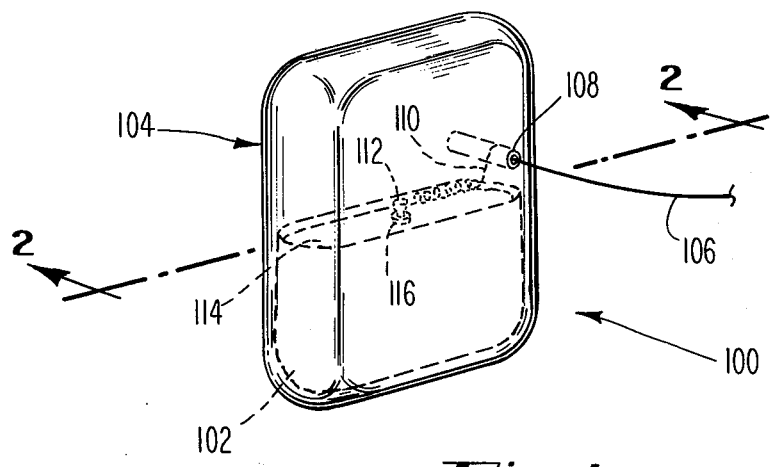
FIG. 1 is a perspective view of the first preferred embodiment of the present invention shown in its actual size.

Referring now to FIG. 1, which is a perspective view showing a first preferred embodiment of the present invention, it may be seen that the pacer, designated generally 100, is comprised of a titanium case 102, a resinous (epoxy) capsule designated generally 104 and an output means for conducting an output pulse from electronic circuit means which are disposed within the titanium case, designated generally 102, to the heart muscle to be stimulated. As shown in FIG. 1, the output means of the present invention generally comprises a probe wire which leads from the pacer to the heart muscle to be stimulated, a socket 108 embedded in the resinous capsule, designated generally 104, for making secure electrical contact with the probe wire 106, a tantalum feed wire designated 110 which contacts the socket 108 at a first end and is welded to a tantalum centerpin 112 at its second end. It will be seen in FIG. 1 that the tantalum center-pin 112 is disposed through the upper surface or lid 114 of the titanium case designated generally 102, said centerpin 112 being encircled by a titanium bushing 116. A grounding plate, not shown in the designated generally 100, and the surrounding body tissue. During the operation of the pacer of the present invention, electronic circuit means for producing a rhythmic heart muscle stimulating negative output pulse, which electronic circuit means is disposed within the titanium case, designated generally 102, produces said rhythmic pulse which is transmitted to the heart muscle to be stimulated by the output means for conducting said output impulse from said electronic circuit means to the heart muscle. A tantalum conductor comprised of the tantalum centerpin 112 and the tantalum feed wire 110 conduct the negative output pulse from the electronic circuit means to the socket 108 where contact is made with the electrode wire 106 which is located at the proper situs in the heart muscle to be stimulated.

Figure 2:
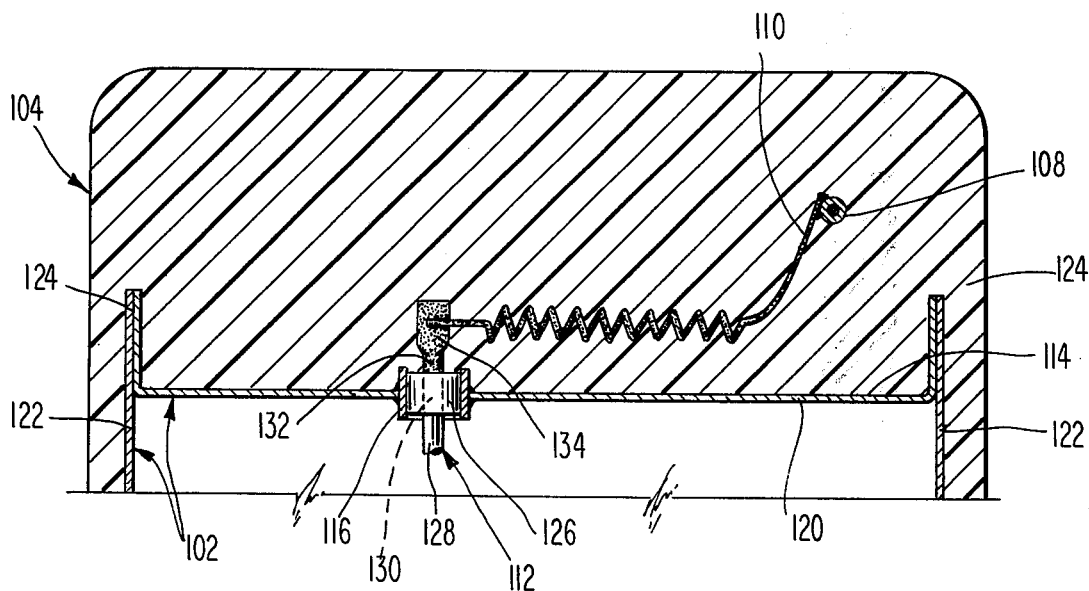
FIG. 2 is an enlarged foreshortened fragmentary view of the embodiment shown in FIG. 1 taken along the lines 2—2 as indicated in FIG. 1.

Referring now to FIG. 2, which is an enlarged foreshortened fragmented cross section of the pacer of FIG. 1, taken as indicated along the lines 2—2 in FIG. 1, the structure of the output means with respect to the pacer may be more clearly seen. The upper surface 114 of the titanium case designated generally 102 may be seen to be formed on the titanium lid 120 of the case. The titanium lid 120 is seen to tightly engage the side walls 122 of the titanium lid 120 is seen to tightly engage the side walls 122 of the titanium case 102 to form a hermetic interface 124 along the engaging portions thereof. It may further be seen that the side walls 122 of the titanium case form a substantially continuous elongated dome-shaped container which, when engaged by the titanium cover 120, form a hermetically sealed enclosure, which enclosure is pierced only by the titanium bushing 116, the ceramic insulator 126 and the tantalum centerpin 112 which are disposed in and through the lid 120. As seen in FIG. 2, the tantalum centerpin 112 has been cut away for purposes of illustration. However, in the pacer of the present invention, the base 128 of the centerpin is connected to the electronic circuit means which is disposed within the hermetically sealed titanium case described above. As also seen in FIG. 2, the mid-portion 130 of the tantalum centerpin designated generally 112 is disposed within the ceramic insulator 126 which engages titanium bushing 116. The ceramic insulator 126 is therefore tubular, acting as an excellent insulator and also a corrosion-resistant seal between the inside of the titanium case and the exterior portion surrounding the neck portion 132 of the tantalum centerpin. As seen in FIG. 2, the mid-portion 130 of the tantalum centerpin, the ceramic insulator 126, and the titanium bushing 116 form a hermetically sealed fitting within the titanium lid 120 of the titanium case designated generally 102. Disposed within the capsule designated generally 104 are the head and neck portions 134 and 132 respectively of the tantalum centerpin designated generally 112, the tantalum feed wire 110 and the socket 108. As seen in greater detail in FIG. 2, the head portion 134 of the tantalum centerpin designated generally 112 is flattened from the substantially cylindrical configuration of the remainder of the tantalum centerpin. This flattened head portion allows a strong weld to be made between the tantalum feed wire 110 and the head portion 134 of the tantalum centerpin. As is seen in FIG. 2, the tantalum feed wire 110 is formed in its mid-portion into the shape of a helix, which shape functions to prevent corrosive materials from easily traveling along the length of the feed wire so as to impinge upon the hermetic seal described above. For the same reason, the tantalum feed wire 110 is selected to have a diameter of 0.3 mm or less, which selection is enabled by the novel aniodic tantalum oxide insulating layer which is shown disposed upon the surfaces of the neck portion 132, head portion 134 and tantalum feed wire 110 representationally by speckling the above named components in the drawings.

In the discussion above and hereinbelow, tantalum is referred to as a preferred material because of its property of forming an insulating oxide layer. However, titanium also has this property, and is preferable for use in the case. In addition, aluminum, niobium, hafnium and like metals may be utilized.

Figure 3A:
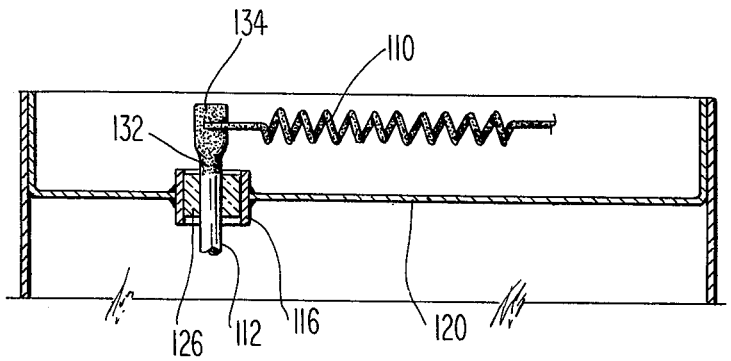
FIG. 3A is an enlarged foreshortened view showing a portion of the case and output means of the embodiment shown in FIG. 1 prior to its encapsulation in an epoxy material.

Referring now to FIG. 3A, which is a fragmentary cross section of the output means of the present invention, it may be seen that the tantalum oxide, $Ta_2O_5$ insulating layer has been disposed upon the surfaces of the neck portion 132, head portion 134 and feed wire 110 prior to the introduction of the epoxy material around those components. In particular, although not clearly illustrated in the drawing, the $Ta_2O_5$ insulating layer is formed on all surfaces of these tantalum components by an aniodic forming process which proceeds as follows: Initially, a tantalum centerpin is selected which may be embedded in a ceramic insulator as shown on the drawings. Tantalum centerpins disposed through ceramic insulators and disposed within titanium bushings are generally commercially available. However, it is necessary to select such a configuration suitable for use in the preferred embodiments as described herein. Following selection of the tantalum centerpin assembly, a suitable tantalum wire stock having a diameter of between 0.01 and 0.6 mm is selected, said wire having a preferable diameter of between 0.01 and 0.3 mm. The tantalum feed wire is then formed by creating a helix or spiral of a desired length in the mid-portion of the wire and by welding the tip of the wire to a relatively flat portion of the head portion 134 of the tantalum centerpin designated generally 112. Since, in the subsequent steps, an aniodic oxide coating is to be formed covering the exposed surfaces not only of the tantalum centerpin and the tantalum feed wire, but also of the weld, applicant prefers the use of tantalum welding electrodes which, upon trace deposition, will not interfere with the crystalline structure of the aniodic oxide layer which is subsequently to be formed. In the absence of tantalum electrodes, applicant believes that welding electrodes of the other metals mentioned above, each of which will form an oxide layer, is preferable to copper which, under adverse circumstances, could tend to interfere with the uniform and continuous $Ta_2O_5$ oxide layer which is to be formed on the exposed surfaces of these components. Following the welding operation, the completed conductor unit comprising the tantalum centerpin welded to the tantalum feed wire is cleaned in order to remove any impurities which may have accumulated on the surfaces thereof. After a thorough cleaning has exposed the bare tantalum metal, the conductor unit is then formed by subjecting the unit to a positive voltage within an electrolytic solution selected from the group consisting of potassium hydroxide, nitric acid, sodium hydroxide, and combinations thereof. General forming techniques are to be applied in obtaining a $Ta_2O_5$ oxide layer which is uniform and continuous over the surfaces of the conductor unit. Generally, applicant has found that excellent results may be obtained by providing a positive voltage over the forming period of between 10 to 64 hours to a maximum voltage of between 35 and 140 volts. As a result of this forming process, a $Ta_2O_5$ insulating layer is produced having a thickness of at least 400 and preferably 500 A per volt.

Tantalum has the property that it can be oxidized in most every electrolyte and is self-healing in such electrolytes by the same process of anodic oxidation, which is why it is a preferred material for use in this invention. In oxidizing tantalum, or any of the other preferred materials, it is preferable to utilize the electrolyte, or the closest approximation thereto, which is going to be present during the actual use of the device. Thus, for a pacer, the prior anodic oxidation is best carried out in sodium or potassium hydroxide, or a mixture thereof. The reason for this is that during the prior oxidation, any impurities that can be eaten out are eaten out and the layer is formed to the desired thickness. In this manner, such impurities are not available to be removed from the layer so as to damage the layer during actual operation. The prior elimination of impurities in the layer substantially reduces a source of leakage current which could otherwise pass through the layer.

Figure 3B:
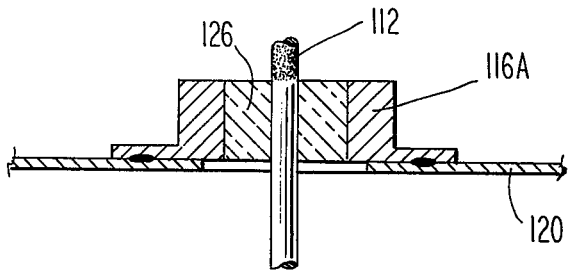
FIG. 3B is a view similar to FIG. 3A, showing an alternate form of seal.

Referring to FIG. 3B, there is shown an alternate form of a seal wherein the titanium bushing 116A has a flange, a bottom portion of the flange being welded to the lid 120. Following the welding of the seal with centerpin 112 to lid 120, the combination may then be anodically oxidized, resulting in the formation of an oxidizing layer on both the exposed portions of centerpin 112 and the lid 120. After this step, the lid is welded to case 102, as previously discussed.

In order to test the effectiveness of various forming processes, the following series of experiments were conducted:

EXAMPLE 1.

Four tantalum foil plates which were 3 × 3 cm square were welded with 30 watt seconds to a 0.3 mm tantalum wire. Each of these plates were cleaned according to a standard method, that is 1½ minutes in Flugene MA ultrasonic, one and a half minutes in Flugene rinse, one and half minutes in Flugene MA ultrasonic, and one and a half minutes in Flugene MA vapor bath. The fully cleaned plates were then stored in a dust free container prior to use. Plate No. 1 was immersed in a 30% potassium hydroxide electrolyte solution and forming was continued for 64 hours at a maximum voltage of 35 volts. The efficiency was approximately 50%, with a weight increase during forming of 0.17 milligrams. Upon completion of the forming process, leakage currents at various voltages were measured to determine the effectiveness of the oxide insulation which was created on the outer surfaces of the tantalum material. At 35 volts, 6.7 microamps of current leakage were present, however, at 20 volts 0.1 microamps were found and at 5 volts 0.00 microamps of leakage occurred. Thus it may be concluded that forming of tantalum in a 30% potassium hydroxide solution produces an extremely effective insulating layer when that tantalum is subjected to voltages in the normal range found within pacers. Additionally, the potassium hydroxide solution did not dissolve the $Ta_2O_5$ oxide layer after its formation, indicating that this oxide layer will resist hydroxides of potassium which might normally impinge on the surfaces of the tantalum wire when implanted in the body cavity.

Plate No. 2 of the four plates originally prepared was formed in 0.01% nitric acid ($HNO_3$). After forming plate No. 2 at a maximum of 35 volts for 64 hours a weight increase of 0.15 milligrams was observed. One hundred percent efficiency was observed to the 35 volt value. In testing for electrical leakage after 64 hours the following values were obtained: at 35 volts there were 80 microamps leakage, at 20 volts 0.98 microamps, and at 5 volts 0.00. Again, no weight change of the oxide layer was observed when subjected to this acid, thereby indicating that the $Ta_2O_5$ oxide layer formed thereby is relatively inert. Although the leakage currents for plate 2 were observed to be somewhat higher than those found when forming took place in 30% potassium hydroxide solution, the figures obtained for leakage in nitric acid are suitable for use in the voltage ranges normally found within pacers.

Plate 3 was formed in a solution comprised of 3% sodium hydroxide and 3% potassium hydroxide. A 50% efficiency was obtained at 35 volts, with a weight increase of 0.15 milligrams. The leakage current after 64 hours at 35 volts was observed to be as follows: at 35 volts 7.43 microamps leakage was observed, at 20 volts 0.19 microamps were found, and at 5 volts no result was obtained. The total weight increase during 64 hours of forming was 0.03 milligrams and the plate turned yellow after the 64 hour period instead of the normal deep blue which is indicative of the presence of a $Ta_2O_5$ oxide layer. A flame test confirmed the suspicion that a deposit of sodium was present in the final oxide layer. The increase in weight after the flame test in a bunsen burner was 1.18 milligrams. Applicants found that it was possible to repair the insulation in nitric acid so that after 5 minutes of repair current at 35 volts the leakage at 35 volts was 24 microamps, at 24 volts was 1.3 microamps, and at 5 volts was 0.00 microamps.

Plate 4 was placed in the flame of a bunsen burner for 10 seconds during which the color temperature of the tantalum plate indicated the plate to be at a temperature of about 1,000° C. The weight increase after 10 seconds in the bunsen burner was 7.58 milligrams. The formation efficiency at 35 volts after that was low according to gasing phenomenon, but only 1/16 of the load of the previous plates was needed, indicating that it was only filling the holes or interstices which remained after the flaming process described above. After ten minutes at 35 volts the leakage current was 13 microamps at 35 volts and 3.0 microamps at 20 volts. It should be noted that this reduction in the leakage current during forming is not as low as normally expected. Generally if a 13 microamp leakage current is experienced at 35 volts, a 0.2 microamp current leakage would be expected at 20 volts. Since the actual leakage found in plate 4 at 20 volts was 3.0 microamps, this experiment indicates that the oxide which was formed by burning differs in its resistance from the oxide which is formed by aniodic oxidation. Applicants believe that more conductive elements are contained within the oxide which is formed by burning, and this theory is confirmed by the fact that when the plate was placed for one and a half hours in a 90° C. 30% NaOH bath 0.07 milligrams was dissolved.

EXAMPLE 2

A second series of investigations was conducted since applicant suspected that the welding technique used in welding the tantalum wire to the tantalum plate produced leakage along the length of the weld. Consequently the tantalum wire was butt welded to a tantalum centerpin feedthrough having a diameter of 0.7 millimeters. By butt welding the tantalum wire with a diameter of 0.3 mm to the larger tantalum centerpin it was possible to reduce the effect of copper residue which was deposited on the weld due to the use of copper welding electrodes. Three plates were prepared as described in Example 1 above, however in this series of tests the forming was conducted to 140 volts in various electrolytes. Instead of carrying the forming process on for 64 hours, as in Example 1, the forming time was reduced to 16 hours throughout this series of tests. A first sample was formed to 140 volts in 0.01% $HNO_3$ (nitric acid). At room temperature the leakage at 140 volts was 50 microamps, at 90 volts was 4.6 microamps and at 10 volts was 0.03 microamps.

Since one of the primary intended end uses of the tantalum wires and centerpins which were being formed in these experiments is as output means carrying negative voltages, during this series of tests applicants also measured the effectiveness of the oxide layer on insulating against leakage of negative voltages. When the sample described above was subjected to a negative voltage of 10 volts, 2.5 microamps leakage was observed after 10 seconds. After 1 minute of negative voltage 3.5 microamps leaked from the sample. Following this negative voltage test, the voltage was again reversed to 140 volts positive at which time a value of 40 microamps after one minute leakage was obtained, and at 10 volts positive 0.00 microamps after 1 minute was observed.

In order to determine the effect of mechanical touching or bending, the sample described above was touched with a pincer and bent several times and then tested at 10 volts positive for leakage. This test is important to determine the suitability of these components for incorporation in pacers where a 10 volt value would normally be experienced. It was discovered that at 10 volts positive after 10 seconds a leakage was observed of 0.20 microamps, and that after 1 minute the leakage had been reduced to 0.10 microamps, thereby indicating that in the presence of a 10 volt positive current there will be substantial repair of a damaged oxide coating.

Following the above test the voltage was again reversed to a 10 volt negative level which, after one minute, showed a leakage value of 3.0 microamps. It should be noted that all the above measurements were taken in 0.01% $HNO_3$ at room temperature. The final weight increase after forming was 0.70 milligrams. In order to check these leakage results, the sample was then tested in a 30% sodium hydroxide solution at 37° C. The leakage current at 20 volts was 2 microamps after one minute and after 16 hours was 0.78 microamps, a weight decrease of 0.08 milligrams was observed over this 16 hour period.

A second sample was formed at 140 volts in 0.01% $HNO_3$ at room temperature. After 16 hours the rest current value was 50 microamps, at 90 volts after one minute was 4.8 microamps, and the weight increase during formation was 0.74 milligrams. This sample was then tested in a 1% sodium hydroxide solution at 37° C at a 20 volt rest current 0.78 microamps leakage was observed after 16 hours. The weight increase during the 16 hour period of 0.02 milligrams was observed, however no color change was seen.

A third sample as described above was formed in 0.01% $HNO_3$ to 140 volts, again for 16 hours. The weight increase observed was 0.72 milligrams with a rest current leakage value being observed of 0.22 microamps at 90 volts. When the sample was placed in a 10% solution of sodium hydroxide a rest current value at 20 volts after 3 hours indicated a leakage of 0.22 microamps without color change. After 20 hours this leakage value decreased to 0.09 microamps.

A fourth sample was again formed in 0.01% $HNO_3$ to 140 volts at a 90 volt rest current, 0.42 microamps leakage was observed and the weight increase was determined to be 0.73 milligrams. When placed in a 1% solution of sodium hydroxide at 37° C a leakage value of 4.0 microamps at 20 volts was observed after 3 hours. Again, no change in color was seen and this leakage value decreased to 2.4 microamps after 20 hours, again with no change in weight.

EXAMPLE 3

Since $Ta_2O_5$ is only formed when the tantalum is subjected to a positive voltage in electrolyte, when bare tantalum is immersed in an electrolyte and subjected to a negative voltage the current which is expected to flow is limited only by the resistance in the circuit, which resistance depends on the surface area of the electrodes and the resistance of the electrolyte solution. Using plates of the above described dimension in a 10% solution of sodium hydroxide at 37°, a current flow of 30 milliamps per millimeter squared is easily obtainable. If, however, a $Ta_2O_5$ oxide insulating layer is first formed by aniodization on the tantalum, in accordance with the method described above, the current flow when subjected to a negative voltage will be substantially less than observed with bare tantalum, and the oxide layer will be found to leak at spots. Applicant conducted tests to determine the amount of leakage to be expected, which tests resulted in a determination that leakage in the order of magnitude of 1 microamp per $millimeter^2$ in 0.01% solution of $HNO_3$ would be expected. In a 10% solution of sodium hydroxide these leakage currents are in the magnitude of 50 microamps per $millimeter^2$, which greater magnitude is explained by the lower resistance of the sodium hydroxide electrolyte. It should be noted that the leakage of an aniodically coated tantalum electrode is in the order of magnitude of 1000 times lower than for bare tantalum.

From the above described tests it may be concluded that a tantalum oxide layer with good isolation properties may be formed using the above described methods. Particularly, when the tantalum component is subjected to a positive charge in sodium hydroxide, potassium hydroxide or sodium chloride solutions, an excellent $Ta_2O_5$ layer is formed which provides more than adequate insulation when subjected to voltages which are a magnitude normally encountered in pacers. Furthermore, it is possible to repair damage of the $Ta_2O_5$ oxide layer and to again obtain sufficient isolation of the component if the tantalum is subjected to a positive voltage. Not only does the $Ta_2O_5$ layer effectively insulate the component against electrical leakage, but it is well suited for use in a pacer as it is inert with respect to sodium hydroxide or potassium hydroxide at body temperatures. Finally, $Ta_2O_5$, when formed on bare tantalum in a thickness of between 400 and 600 and preferably 500 A acts to insulate the tantalum wire when subjected to negative voltages. In particular, the degree of insulation of $Ta_2O_5$ coated tantalum wire is approximately 1,000 times better than that of bare tantalum.

EXAMPLE 4

Heretofore, stainless steel has been employed as the casing material for heart pacers, except in those rare instances where the strength and weight characteristics of titanium make it the metal of choice. Applicant is unaware of any instance where titanium has been selected or used for its electrical properties. By way of comparing titanium to tantalum, the following tests were performed:

A plate of titanium was placed in a rising positive voltage after immersion in a 0.9% sodium chloride solution, said voltage being increased to maintain a current density which was 1 milliamp per $centimeter^2$. At 10 volts, no further rise in voltage was obtained. A similar test was conducted substituting a 10% solution of sodium hydroxide for the sodium chloride solution used above. The results in sodium hydroxide did not differ substantially from those in sodium chloride, with a maximum voltage of 10 volts being obtained.

In another series of tests, a titanium plate of 20 centimeters square area was placed in a 0.9% sodium chloride solution at 37° C. and subjected to a positive voltage of 8.3 volts. After one and a half hours the leakage current observed was 10.4 milliamps, and after 48 hours the leakage current had been reduced to 5.0 milliamps. When compared to the tantalum oxide results described above, it may be seen that titanium does not form a continuous oxide layer having the superior insulating properties of tantalum.

In another test, another titanium plate of 20 $cm^2$ was immersed in a solution of 0.9% sodium chloride at 37° C. and was subjected to a voltage of 4.77 volts. After one and a half hours, leakage was measured in the amount of 0.317 milliamps, and after 48 hours the leakage current was 67 microamps. As a result of the above it was concluded that the lower voltage formation of the titanium plate produced a superior oxide layer.

Finally, in this series of tests, two titanium plates were immersed in a 0.9% sodium chloride solution at 37° C. and were subjected to a positive voltage of 5.4 volts. After 10 minutes the leakage current observed was 2.5 milliamps, after 16 hours the leakage current was 250 microamps, and after 24 hours the leakage current had been reduced to 150 microamps. Forming was continued and after 48 hours the leakage current was 100 microamps and after 86 hours the leakage current was 60 microamps.

From the above test it was concluded that the insulating layer which was obtainable by oxidation of titanium using the above method did not favorably compare to the insulating layer obtained by tantalum, however, when used to isolate titanium components in a heart pacer in combination with other tantalum components the insulation which is obtained from such an oxide layer may be considered to be adequate. Consequently, the use of a system having a tantalum centerpin, a titanium bushing and a titanium can would be ideal in terms of limiting the electrical leakage of current during the useful life of the heart pacer.

EXAMPLE 5

In order to simulate the actual heart pacer situation the following tests were conducted:

An actual heart pacer was connected in series with seven batteries. The negative output pulse of the pacer was directed through a tantalum plate which was immersed in a 10% sodium hydroxide solution, which solution was analytically pure, having been made up from doubly distilled water. The pacer pulse was set at a 1 millisecond pulse width having a maximum voltage of 10 volts. The positive side of the batteries were connected in parallel to two tantalum plates which were also suspended in the electrolyte solution, and a titanium plate suspended in the solution was connected to the circuit between the negative terminal of the batteries and the positive terminal of the pacer. As a control, a tantalum plate which was not connected to the circuit was suspended in the solution. Before and after the ensuing test the weight of the tantalum plates was checked. During the test period the current was monitored. Of the four tantalum plates the largest weight loss was 0.00017 grams ±0.00003 grams and the smallest weight loss was 0.00006 grams ± 0.00003 grams. Thus it was concluded that the weight loss was so minor that little or no problem will occur due to the actual physical deterioration of the tantalum material.

This test was conducted for a period of 500 hours and leakage current readings were taken at 1, 3, 100 and 500 hours. For the two tantalum plates which were subjected to a positive charge the total leakage after one hour was 0.91 microamps, after 3 hours 0.52 microamps, after 100 hours 0.11 microamps, and after 500 hours 0.05 microamps. It was consequently concluded that the leakage current of positive tantalum plates wherein the tantalum is 99.999% pure K-grade is and will remain very low during the operating life of a pacer. The tantalum plate which was connected to the negative output pulse of the pacer was observed to have a current limit of 10 milliamps after 1 hour, 2.1 milliamps after 3 hours, 0.15 milliamps after 100 hours and 0.03 milliamps after 500 hours. As expected the current readings for this plate decreased over the test period as a result of the oxidation of the titanium plate which was connected to the positive side of the pacer. Consequently applicant concluded that the use of a titanium can with a tantalum output means will provide a heart pacer which is not prone to electrical leakage.

EXAMPLE 6

By way of comparison applicant repreated the test described in the above sample in order to determine the effect of using a stainless steal electrode in place of the titanium electrode of the previous example. Since pacers are normally constructed with stainless steel cases, and not with titanium cases, this configuration will test the effectiveness of the novel tantalum output means of the present invention with the more conventional stainless steel case material. As in the last test a pacer which was said to produce a 1 millisecond output pulse limited to 10 milliamps was connected, as before, to square tantalum plates having 30 cm on a side, two of which plates were connected to the positive side of the batteries and a third of which plates was connected to the negative output terminal of the pacer. Also as before, these plates were formed prior to this test to a voltage of 140 volts (positive) in order to form a $Ta_2O_5$ layer having a thickness of approximately 0.24 micrometers. Each of the three tantalum plates directly involved in the test over a 500 hour period gained between 0.00014 grams ±0.00003 grams and 0.00047 grams ±0.0003 grams. After a test period of 500 hours the current limit remained 10 milliamps, which was the current limit set for the pacer at the beginning of the test. From this information applicant concluded that titanium possesses superior insulating qualities for use in the case of a heart pacer, and is definitely preferred over stainless steel. This is particularly true in light of the fact that the electrode corroded in the presence of stainless steel and that all of the plates experienced a slight weight increase due to the deposit of solved material from the stainless steel electrode.

Referring again to FIG. 3 of the drawings, it may be seen that the tantalum centerpin designated generally 112 and the tantalum feed wire 110 have already disposed thereon the $Ta_2O_5$ oxide coating formed by the processes described above. Following formation of this $Ta_2O_5$ oxide layer on these components, the tantalum centerpin designated generally 112 is connected to the electronic circuit means of the heart pacer and the case including that electronic circuit means is assembled to form a hermetic seal therewithin. Finally, the tantalum centerpin 112 and tantalum feed wire 110 are encapsulated within the epoxy capsule designated generally 104 in FIG. 2.

Figure 4:
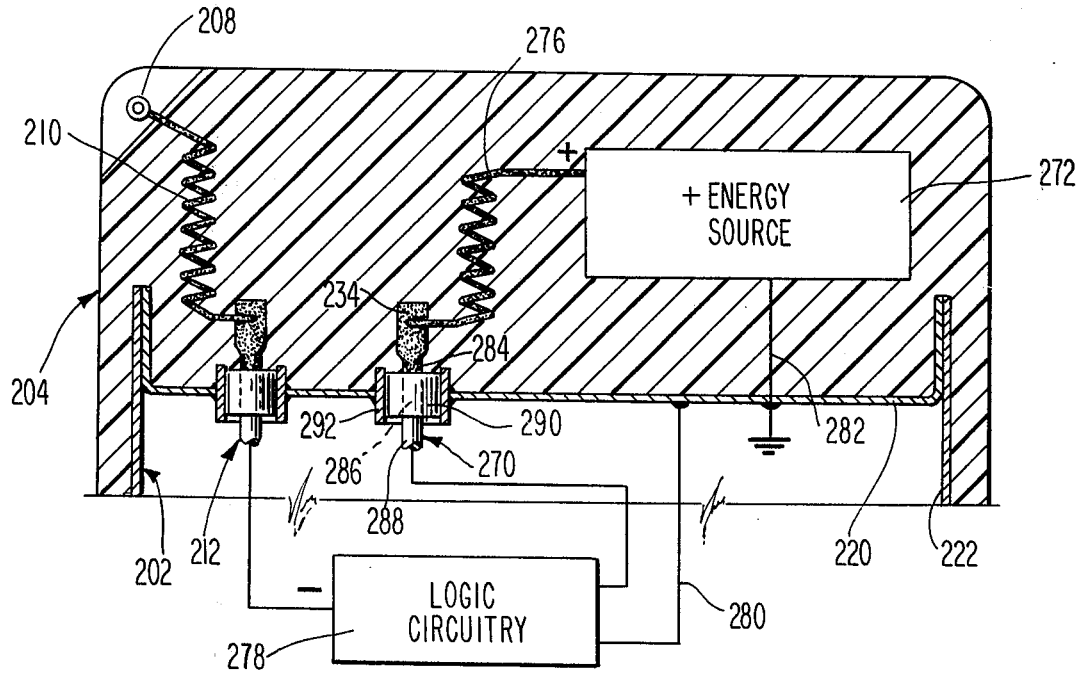
FIG. 4 is an enlarged cross section similar to the view shown in FIG. 2 of a second preferred embodiment of the present invention showing the disposition of an energy source and input means outside of the titanium case but within the capsule of the present invention.

Referring now to FIG. 4, which shows a cross section of an alternate preferred embodiment of the present invention, the epoxy capsule designated generally 204 may be seen to surround the titanium case designated generally 202. The cover or lid 220 of the titanium case forms a hermetic seal with the side walls 222 of the case in a manner similar to that described in the previous embodiment. However, unlike the other preferred embodiment, the titanium cover 220 has disposed therein two tantalum centerpins, a first output centerpin designated generally 212 and a second input centerpin designated generally 270. As in the embodiment previously described, the output centerpin designated generally 212 comprises a portion of the output means of the present invention including a tantalum feed wire 210 and a socket 208. As a result, the output means shown in the embodiment of FIG. 4 is in all operative respects similar to the output means shown and described above, except that the socket 208 and feed wire 210 are disposed so that connection with the probe wire is made near a rounded corner of the resinous capsule designated generally 204. The input centerpin designated generally 270 which is also disposed through the cover 220 of the tantalum case may be seen to be connected to an energy source 272 which is represented diagrammatically. In actual practice, the energy source 272 is comprised of batteries which, due to their chemical configuration, may have a tendency to leak electrolyte to some degree during the expected ten plus year useful life of the pacer. Connecting the head portion 234 of the input centerpin designated generally 270 with the energy source 272 is a tantalum wire 276 having formed on the outsides thereof an aniodic continuous $Ta_2O_5$ layer. Together the tantalum wire 276, the input centerpin designated generally 270, the weld between the tantalum wire and the input centerpin (not shown in the drawings) and the aniodic oxide coating covering the exposed surfaces of these elements comprise the conduit means for electrically connecting the energy source to logic circuitry which is disposed within the hermetically sealed titanium case. This logic circuitry 278, when energized, produces the rhythmic heart muscle stimulating negative output pulse which is carried by the output means previously described. The titanium case designated generally 202 acts as the system reference for the circuitry, and the titanium case is shown diagrammatically connected to the logic circuitry and energy source by grounding leads 280 and 282 respectively. Not shown on the diagrammatic circuit in FIG. 4 is the electrical connection which is made by a body plate between the system reference and the body fluids surrounding the implanted pacer. As described in the previous embodiment, the configuration of the input centerpin, designated generally 270, is similar to that of centerpins used in the output means of the present invention, comprising head portion 234, neck portion 284, mid-portion 286, base portion 288 and ceramic insulator 290. As in the other embodiments, a titanium bushing 292 is disposed through the cover 220 and surrounds and forms a hermetic seal with the ceramic insulator 290.

As described in the above examples, the novel input or conduit means of the present embodiment, which means electrically connects the energy source to the logic circuitry through the titanium cover, minimizes the electrical leakage which is likely to occur from the tantalum components to the case. Since the conduit or input means shown in FIG. 4 is positively charged, this input means has the extra advantage of being able to repair minor imperfections or damage which reduce or destroy small portions of the $Ta_2O_5$ oxide layer disposed thereon. As with the other embodiments of the present invention, and as also demonstrated in the examples, the tantalum output means of the embodiment shown in FIG. 4 is negatively charged with respect to the titanium case. The lid 220 of case 202 may be aniodically oxidized along with the connectors, prior to being welded to the remainder of the case. As described above, any leakage which does occur through the aniodic $Ta_2O_5$ insulating layer disposed on the surfaces of that output means will tend to further oxidize the titanium case, thereby reducing the electrical leakage between the insulator and case to an infinitesimal amount. Finally, and perhaps most importantly, in the embodiment shown in FIG. 4, the energy source is disposed within the epoxy material in such a way as to virtually eliminate the possibility that leaking battery electrolyte could cause a malfunction in the logic circuitry, which logic circuitry is hermetically sealed within the titanium case. In particular, the location of the energy source, the helical configuration of the tantalum wire 276, the configuration and location of the tantalum centerpin designated generally 270, the selection of relativey inert insulator such as the ceramic insulator 290, and the disposition of the titanium bushing 292 in the titanium cover 220 all act to produce a safe and corrosion resistant heart pacer.

It is understood that the invention disclosed herein is generally applicable to medical electronic devices which are designed for operation within a physiological system, and in particular, a human system. The forming of an oxidation layer on tantalum, titanium, aluminum, hafnium, niobium and like metals is applicable wherever there are components within the device across which a potential may exist some or all of the time, and across which there is otherwise a chance of leakage current flowing. By so oxidizing the surface of the positive component, the leakage is effectively eliminated. Thus, the invention extends to battery cases, signal terminals of whatever configuration and leads connected thereto, discrete components or packages which carry a potential, etc. The thickness of the oxidation layer in accordance with this invention is about 14 A per volt. Corresponding to oxidizing at between about 30 volts and 140 volts, the resultant oxidation layer is in the range of about 400 A to 2000 A. In practice, a factor of 3 has been found to effectively eliminate leakage current, i.e., to guard against leakage in a device where potential differences at 30 volts. As used in the claims following hereinbelow, a layer of a given voltage corresponds to a layer formed at such given voltage.

I claim:

1. An insulated, corrosion-resistant pacer for rhythmically stimulating heart muscle, comprised of:
   a. a hermetically sealed case;
   b. electronic circuit means for producing a rhythmic heart muscle stimulating negative output pulse, said electronic circuit means being disposed within said case and including a power source providing an operating voltage;
   c. output means for conducting said output pulse from said electronic circuit means to outside of said case, said output means extending from within said case to a terminal outside of said case and comprising a tantalum centerpin disposed through said case and a tantalum feed wire welded to said centerpin, and having an anodically formed substantially continuous $Ta_2O_5$ insulating layer covering said feed wire, the portion of said centerpin which is outside of said case, and the surface where said feed wire is welded to said centerpin; and
   d. epoxy capsule means for surrounding said output means;

whereby said insulating layer reduces electrical leakage from said conductor to said case, and whereby said insulating layer further protects said pacer from corrosive and electrolytic attack.

2. The invention of claim 1 wherein said case is substantially composed of a metal which forms an anodic oxide layer thereon in the presence of said output pulse.

3. The invention of claim 1 wherein at least a portion of said feed wire is in the form of a helix.

4. The invention of claim 3 wherein said output means further comprises a titanium bushing disposed around said centerpin and insulated therefrom by a ceramic insulator.

5. The invention of claim 1 wherein said $Ta_2O_5$ insulating layer is substantially pure, having a thickness of at least 400 A.

6. The invention of claim 1, comprising a tantalum weld between said centerpin and said feed wire.

7. In a pacer for rhythmically stimulating heart muscle, said pacer having a hermetically sealed titanium case, which case contains electronic circuit means for producing a rhythmic heart muscle stimulating negative output pulse and a tantalum output means for conducting said output pulse from said electronic circuit means to said muscle; the improvement comprising: an anodically formed substantially continuous $Ta_2O_5$ insulating layer disposed on the surfaces of said tantalum output means, wherein a portion of said titanium case surrounding said tantalum output means has an anodically formed insulating oxide layer.

8. The pacer of claim 7, wherein said output pulse has a predetermined voltage magnitude of up to 10 volts, and said layer has a thickness of at least about 400 A.

9. In making a pacer for rhythmically stimulating heart muscle, said pacer having a hermetically sealed titanium case, said case having a lid and containing therein electronic circuit means for producing a rhythmic heart muscle stimulating output pulse and a tantalum output means for conducting said output pulse from said electronic circuit means to outside of said case, the method of assembly of said pacer comprising the steps of: forming an oxide insulating layer on both said lid and predetermined surfaces of said tantalum output means and encapsulating said insulated surfaces.

10. The method of claim 9 wherein said insulating layer is formed by a method comprising the steps of
   a. immersing at least a portion of said output means in an electrolytic solution; and
   b. applying a positive voltage to said output means to anodically form said $Ta_2O_5$ insulating layer on said output means.

11. The method of claim 10 wherein said electrolytic solution is comprised of a combination of sodium hydroxide and potassium hydroxide.

12. The invention of claim 10 wherein said pacer has a predetermined supply voltage, and said positive voltage during formation is at least about 3 times the supply voltage of said pacer.

13. The invention of claim 12 wherein said positive voltage during formation is between 35 and 140 volts.

14. The method of claim 10 wherein said forming is continued for a sufficient length of time to produce an insulating layer having a thickness of at least about 14 A per volt.

15. The method of claim 10, comprising choosing said electrolytic solution as a close approximation of the body fluid in which a pacer is implanted.

16. The method of claim 9, further comprising connecting said output means to said lid prior to assembly of said pacer, forming said insulating oxide layer on said lid and output means, and hermetically sealing said lid to said case.

17. The method of claim 16, comprising welding said output means to said lid, and wherein said oxide layer covers said welded connection.

18. In a medical electronic device adapted for implantation in a human body, said device having at least a first surface area electrically separated from a second surface area, and means for placing said first area at a negative potential of a predetermined voltage with respect to said second area, the improvement consisting of said first area being comprised of a first predetermined metal and said second area being comprised of a second predetermined metal said first surface area and at least a portion of said second surface area having thereon an anodically formed oxidation layer 19. The device as described in claim 18, wherein said oxidation layer thickness is in the range of 400 A to 2000 A.

20. The device as described in claim 18, wherein said predetermined voltage is in the range of 4 to 8 volts.

21. The device as described in claim 18, wherein said secondary is comprised of a second metal, said first and second metals belonging to a predetermined group of like metals.

22. The device as described in claim 21, wherein said first metal is tantalum and said second metal is titanium.

23. A pacer for rhythmically stimulating heart muscle, said pacer comprising a hermetically sealed case of a first predetermined metal, and electronic circuit means contained within said case for producing a rhythmic heart muscle stimulating negative output pulse; output means comprising a second predetermined metal for conducting said output pulse from said electronic circuit means to a point outside of said case; and anodically pre-formed oxide insulating layers disposed on predetermined surfaces of said output means and on at least a portion of the outside of said case surrounding said output means.

24. A pacer for rhythmically stimulating heart muscle, comprising:
   a. a hermetically sealed titanium case;
   b. electronic circuit means for producing a rhythmic heart muscle stimulating negative output pulse, said circuit means being contained within said case;
   c. energy source means for providing energy to said electronic circuit means;
   d. connecting means, for electrically connecting said energy source means and said electronic circuit means;
   e. output means for conducting said output pulse from said electronic circuit means to outside of said case, said output means having a tantalum conductor extending from inside of said case outside of said case;
   f. said tantalum conductor portion outside of said case and a portion of said case surrounding said tantalum conductor having disposed thereon an anodically formed oxide insulating layer; and
   g. said tantalum conductor portion having a first element which extends through said case and a second element constituting a feed wire in the form of a helix, said first and second elements being integrally joined.

25. The pacer as described in claim 24, comprising encapsulating means for encapsulating said pacer so that said tantalum portions of said output means is embedded in resinous material, said output means comprising a terminal element connected to said tantalum portion and providing access for external connection thereto.

26. The pacer as described in claim 24, wherein said output means comprises a titanium bushing around said tantalum conductor, said bushing being welded to said case.

27. The pacer as described in claim 24, comprising a tantalum weld connecting said first and second elements.

28. A pacer for rhythmically stimulating heart muscle, said pacer comprising a power source, electronic circuit means connected to said power source for producing rhythmic heart muscle stimulating output pulses, a hermetically sealed titanium case containing said electronic circuit means, and output means for conducting said output pulses from within said titanium case to outside of said case, said output means having a tantalum feedthrough element extending through said case and a titanium bushing integrally connected to said case, said feedthrough element and said titanium bushing each having an oxide layer disposed on the surface thereof outside of said case.

29. The pacer as described in claim 28, comprising an anodically pre-formed oxide layer disposed on a portion of said titanium case surrounding said tantalum output means, on said tantalum feedthrough element and on said titanium bushing.

30. The apparatus as described in claim 29, wherein said case also contains said power source.

31. A medical electronic device adapted for implantation in a human body, said device comprising a hermetically sealed case of a first predetermined metal, and electronic circuit means contained within said case for producing electrical signals; and feedthrough means for providing an electrical conduction path between said electronic circuit means and a point outside of said hermetically sealed case, said feedthrough means comprising insulating means for insulating said electrical conduction path from said case and bushing means for interfacing said insulation means with said case, said bushing means being made of said first predetermined metal and having an anodically formed oxide insulating layer disposed on at least the outside surfaces thereof.

32. The device as described in claim 31, wherein said predetermined metal is titanium and said bushing means comprises a titanium bushing.

33. The device as described in claim 32, comprising connection means for connecting said electronic circuitry to said feedthrough means and to said case such that signals delivered from said circuit means are positive at said bushing with respect to said feedthrough pin.

34. The device as described in claim 32, wherein said feedthrough means comprises a tantalum centerpin which provides said electrical connecting path.

* * * * *

UNITED STATES PATENT OFFICE
CERTIFICATE OF CORRECTION

Patent No. 4,010,759     Dated March 8, 1977

Inventor(s) Gerard B. M. Boer

It is certified that error appears in the above-identified patent and that said Letters Patent are hereby corrected as shown below:

Column 2, line 41, before "interfere", delete "the" and insert therefor --and--.

Column 4, line 27, after "shown in the", insert --drawings, produces electrical contact between the pacer,--.

Column 4, beginning on line 51, delete "lid 120 is seen to tightly engage the side walls 122 of the titanium".

Column 12, line 24, delete "$\pm 0.0003$" and insert therefor --$\pm 0.00003$--.

Column 14, line 31, after "differences", insert --of up to 10 volts are present, a layer is formed by oxidizing--.

Signed and Sealed this fifth Day of July 1977

[SEAL]

Attest:

RUTH C. MASON
*Attesting Officer*

C. MARSHALL DANN
*Commissioner of Patents and Trademarks*